(12) United States Patent
Grange et al.

(10) Patent No.: US 8,739,622 B2
(45) Date of Patent: Jun. 3, 2014

(54) CAPACITIVE HUMIDITY DETECTOR WITH NANOPOROUS HYDROPHILIC DIELECTRIC

(75) Inventors: Hubert Grange, Grenoble (FR);
Jean-Sébastien Danel, Echirolles (FR);
Brigitte Desloges, Reymure de Vif (FR);
Vincent Jousseaume, Le Sappey en Chartreuse (FR)

(73) Assignee: Commissariat a l'Energie Atomique et aux Energies Alternatives, Paris (FR)

(*) Notice: Subject to any disclaimer, the term of this patent is extended or adjusted under 35 U.S.C. 154(b) by 573 days.

(21) Appl. No.: 13/054,322

(22) PCT Filed: Jun. 22, 2009

(86) PCT No.: PCT/EP2009/057708
§ 371 (c)(1),
(2), (4) Date: Apr. 14, 2011

(87) PCT Pub. No.: WO2010/006877
PCT Pub. Date: Jan. 21, 2010

(65) Prior Publication Data
US 2011/0179861 A1    Jul. 28, 2011

(30) Foreign Application Priority Data
Jul. 16, 2008 (FR) .................................. 08 54826

(51) Int. Cl.
*G01N 27/00* (2006.01)
(52) U.S. Cl.
USPC ...................................... 73/335.04; 73/29.01
(58) Field of Classification Search
USPC .......................................... 73/335.04, 29.01
See application file for complete search history.

(56) References Cited

U.S. PATENT DOCUMENTS

| | | | |
|---|---|---|---|
| 4,438,480 A | 3/1984 | Chambaz et al. | |
| 4,532,016 A | 7/1985 | Chambaz et al. | |
| 5,143,696 A | 9/1992 | Haas et al. | |
| 6,356,087 B1 | 3/2002 | Wallrafen | |
| 6,479,110 B2 | 11/2002 | Grill et al. | |
| 8,075,730 B2 * | 12/2011 | Shimura et al. | 156/345.32 |
| 2003/0179805 A1 | 9/2003 | Hamamoto et al. | |
| 2004/0156987 A1 | 8/2004 | Yim et al. | |
| 2004/0177685 A1 | 9/2004 | Yokura et al. | |

(Continued)

FOREIGN PATENT DOCUMENTS

FR    2 486 656        9/1980
FR    2 893 761 A1     5/2007

(Continued)

OTHER PUBLICATIONS

International Search Report issued Aug. 25, 2009, in Application No. PCT/EP2009/057708.

(Continued)

*Primary Examiner* — Hezron E Williams
*Assistant Examiner* — Rodney T Frank
(74) *Attorney, Agent, or Firm* — Oblon, Spivak, McClelland, Maier & Neustadt, L.L.P.

(57) ABSTRACT

A humidity sensor of capacitive type, a device for detecting or measuring humidity including the sensor, and a method to fabricate the sensor. The humidity sensor includes at least one nanoporous dielectric material positioned between at least one first electrode of a capacitor and at least one second electrode of the capacitor.

13 Claims, 15 Drawing Sheets

(56) References Cited

U.S. PATENT DOCUMENTS

| | | |
|---|---|---|
| 2004/0207083 A1 | 10/2004 | Giles |
| 2007/0161256 A1 | 7/2007 | Gates et al. |
| 2008/0316673 A1 | 12/2008 | Hoofman et al. |
| 2009/0141767 A1 | 6/2009 | Cummins |
| 2009/0203225 A1 | 8/2009 | Gates et al. |

FOREIGN PATENT DOCUMENTS

| | | |
|---|---|---|
| JP | 62-285054 | 12/1987 |
| JP | 2006-032568 | 2/2006 |
| JP | 2006-058084 | 3/2006 |
| JP | 2006-200004 | 8/2006 |
| JP | 2007-005324 | 1/2007 |
| JP | 2007-158000 | 6/2007 |
| JP | 2008-039550 | 2/2008 |
| WO | WO 2007/036922 A1 | 4/2007 |
| WO | WO 2007/057794 A1 | 5/2007 |

OTHER PUBLICATIONS

French Preliminary Search Report issued Feb. 24, 2009, in Application No. FR 0854826 (FA 710910).

Mikko Björkqvist, et al., "Studies on Hysteresis Reduction in Thermally Carbonized Porous Silicon Humidity Sensor", IEEE Sensors Journal IEEE USA, vol. 6, No. 3, XP-002516517, Jun. 2006, pp. 542-547.

H. Grangé, et al., "Polymer-Based Capacitive Hygrometers", Chemical Sensor Technology, vol. 3, N. Yamazoe, Ed.,Kodansha Ltd., 1991, pp. 147-162.

M. Yamana, et al., "Porous Silicon Oxide Layer Formation by the Electrochemical Treatment of a Porous Silicon Layer", J. Electrochem Soc., vol. 137, No. 9, Sep. 1990, pp. 2925-2927.

J. Salonen, et al., "Sub-ppm moisture detection with a simply thermally carbonized porous silicon sensor", Sensors and Actuators B 114, Elsevier 2006, pp. 423-436.

A. Grill, et al., "Ultralow-k dielectrics prepared by plasma-enhanced chemical vapor", Applied Physics Letters, vol. 79, No. 6, August pp. 803-805.

Raymond N. Vrtis, et al., "Plasma Enhanced Chemical Vapor Deposition of Porous Organosilicate Glass ILD Films With k≤2.4." Mat. Res. Soc. Symp. Proc., vol. 766, 2003, pp. 259-264 (E7.4.1-E.7.4.6).

V. Jousseaume, et al., "Porous ultra low k deposited by PECVD: From deposition to material properties", Surface & Coatings Technology 201, 2007, pp. 9248-9251.

English translation of Japanese Office Action, dated Jun. 4, 2013, issued in counterpart Japanese Patent Application No. 2011-517839. 4 pages.

* cited by examiner

CAPACITIVE HUMIDITY DETECTOR WITH NANOPOROUS HYDROPHILIC DIELECTRIC

TECHNICAL FIELD

The invention relates to the field of humidity detecting and/or measuring devices, in particular to humidity sensors of capacitive type.

It concerns an improved humidity sensor device with nanoporous dielectric material allowing the detection of low humidity levels, and a method to fabricate said sensor.

It also provides for a differential device to measure humidity using said sensor.

The invention notably applies to the detection of humidity in encapsulated components such as integrated circuits, MEMS or NEMS.

STATE OF THE PRIOR ART

There are a large number of existing techniques and components to carry out measurement of humidity levels.

The components used are generally adapted for measuring relative humidity from 0% to 100% RH.

Throughout this description, the term relative humidity RH shall be used to designate the ratio between the quantity of water vapour contained in a given medium and the maximum quantity which could be contained therein (saturation point) at a given temperature, this ratio being expressed by an RH number varying between 0 and 100.

Humidity measurement devices for measuring between 0 and 100% RH that are commonly used are: lithium chloride hygrometers, psychrometers, mass spectroscopes, condensation hygrometers, humidity measurement devices measuring variation in impedance.

Measurement of relative humidity by measuring the variation in impedance is the most frequently used, since it is the easiest to implement.

In particular, there are two categories of sensors measuring variation in impedance.

A first category concerns sensors of a variation in resistance, in which the variation in conductivity of a surface is measured.

Sensors of capacitive type can also be distinguished, in which a layer of sensitive dielectric material is provided to absorb surrounding humidity. In said sensor, the layer of dielectric material is located between two electrodes and forms a capacitor. When humidity varies, the quantity of water absorbed by said layer of dielectric material also varies, leading to a change in the dielectric constant of this layer, and to a variation in the capacitance of the capacitor which is measured. This variation may be substantial due to the high value of the dielectric constant of water which is of the order of 80.

In a sensor of capacitive type, the electrodes of the capacitor may be in the form of combs made of metal for example such as AlCu, AlSi, or CrNiAu. The 2 electrodes of the capacitor may be distributed over one same plane such as described for example in document US 2004/0 177 685 or document US 2003/0 179 805. Document U.S. Pat. No. 6,356,087 describes a capacitive sensor provided with electrodes distributed over different planes and facing one another.

In a humidity sensor of capacitive type, one of the electrodes may be permeable to humidity, to allow the water vapour to migrate into the layer of dielectric material of the capacitor. This permeable electrode may be of narrow thickness e.g. in the order of 10 to 20 nm, and may be in gold or constrained Cr so as to cause cracks in the material and thereby promote more rapid diffusion of the water vapour to improve the response time of the sensor.

One example of a humidity sensor containing a polymer with an upper Cr electrode is given in document FR 2 486 656 and in the document: "Polymer Based Capacitive Hygrometers", H. Grange and G. Delapierre, Chemical Sensor Technology, Vol. 3, N. Yamazoe, Ed., Kodansha Ltd., pp. 147-162, (1991).

In general, the chief criteria that are sought for a humidity sensor are:

very short response time,
linear response in relation to relative humidity (RH) between 0 and 100% RH,
low hysteresis,
low temperature coefficient,
broad temperature operating range, preferably between −20° C. and 80° C.,
measurement stability over time, including in a harsh medium.

Some humidity sensors are provided to measure very low humidity levels: typically from 10 ppm (0.001%) to 1,000 ppm (0.1%).

For example, a humidity value of 40% RH at 23° C. in air corresponds to a proportion of water of 1% or 10,000 ppm in air.

For some applications, precise measurement or precise detection of small quantities of humidity may prove necessary.

Among the techniques used to perform said detection is mass spectrometry. This method is not simple to use and cannot be used on an industrial scale.

Surface conductivity sensors can also be used for low hygrometry measurements. The measurement principle is then based on the detection of an inter-electrode leakage current from a polarised sensor subjected to a cooling heat cycle. The dew point corresponds to the start of conduction. The corresponding temperature can be converted into humidity content in ppmv. The drawback of this method is the need to set up a cooling system at the component in order to obtain a progressive reduction in surface temperature.

The document: "Porous Silicon Oxide layer formation by the electrochemical treatment of a porous silicon layer" by Yamana et al. Electrochemical Society, vol. 137, 1990 presents a humidity sensor designed for low hygrometry measurements and comprising a microporous $SiO_2$ layer.

The document: "Sub ppm trace moisture detection with a simple thermally carbonized porous silicon sensor", by Salonen et al. Elsevier, 2005, discloses a humidity sensor intended to perform measurements of low levels of humidity, and provided with a SiC microporous layer.

In either one of these sensors, having regard to pore size, water saturation is not achieved for intermediate humidity levels of between 55% and 97%. Below 55% RH, the sensitivity of the sensors is not satisfactory.

The problem arises of finding a new humidity sensor with improved sensitivity, designed for the detection of low humidity levels, and which does not have the above-mentioned shortcomings.

DISCLOSURE OF THE INVENTION

The invention concerns the providing of a highly sensitive humidity detecting and/or measuring device, in particular for the detection and/or measurement of low levels of humidity.

By "low humidity level", is meant relative humidity of less than 55% RH and more particularly less than 20% RH.

For this purpose, the invention proposes a detector of capacitive type, comprising at least one dielectric material arranged between at least one first electrode and a second electrode, with pores having a radius less than 2 nm.

With said dielectric, it is possible to obtain improved sensitivity.

The nanoporous dielectric may be a "low-k" dielectric such as those usually used in the field of interconnects.

The nanoporous dielectric may be in MSQ for example or SiOCH. Said nanoporous dielectric materials have high sensitivity to low humidity of between 0 and 20% relative humidity.

The nanoporous material may comprise hydrophilic sites. The nanoporous material may have undergone treatment, for example, so that it becomes hydrophilic or more hydrophilic. Hydrophilic treatment by oxidation of the nanoporous material may have been conducted for example.

Said oxidation of the nanoporous material may be performed using oxidizing plasma treatment. Plasma using $N_2O$ may advantageously be used.

The hydrophilic sites may be of SiO, SiOH or Si* type (radical Si), in particular when the nanoporous dielectric is MSQ or SiOCH.

By increasing the hydrophilic nature of the sensor, it is possible to increase the sensitivity thereof.

The sensor may further comprise at least one floating electrode permeable to humidity and resting upon the nanoporous material, the floating electrode being positioned facing said first electrode and said second electrode.

One application of the sensor is the detection of leaks in encapsulated components of integrated circuit type, MEMS or NEMS and comprising a closed or sealed cavity in which humidity is measured.

According to one possible embodiment, the sensor may comprise several layers of different nanoporous materials between the electrodes.

The invention also concerns a device for measuring or detecting humidity, comprising a sensor of capacitive type comprising at least one nanoporous dielectric material arranged between at least one first electrode and a second electrode, and a capacitor comprising a non-porous dielectric material.

The pores of the nanoporous dielectric material may have a radius of less than 2 nm.

By non-porous dielectric material is meant that it does not contain any open porosity.

The capacitor may be arranged so that it shares a common electrode with said capacitive sensor.

Said nanoporous dielectric material of the sensor of said device may be MSQ or SiOCH.

Said nanoporous dielectric material may have been subjected to hydrophilic treatment using oxidizing plasma.

The invention also concerns a method to fabricate a humidity sensor of capacitive type, comprising:
   forming, on a substrate, at least one first electrode and at least one second electrode,
   forming at least one nanoporous dielectric material at least between said first electrode and said second electrode, said nanoporous dielectric material having pores with radius of less than 2 nanometers.

According to one possible embodiment, the nanoporous dielectric material may be MSQ or SiOCH.

The method may further comprise: the creation of hydrophilic sites on said nanoporous material.

This step can be conducted by performing a treatment step e.g. oxidizing the nanoporous material.

The creation of hydrophilic sites on said nanoporous material may be carried out by oxidizing said material using $N_2O$ plasma.

The method may further comprise: forming at least one floating electrode permeable to humidity on the nanoporous material, and positioned facing said first electrode and said second electrode.

BRIEF DESCRIPTION OF THE DRAWINGS

The present invention will be better understood on reading the description of examples given solely for illustration purposes and in no way limiting, with reference to the appended drawings in which.

Identical, similar or equivalent parts in the different figures carry the same reference numbers to facilitate cross-reading between the figures.

The different parts shown in the figures are not necessarily drawn to scale for better legibility of the figures.

DETAILED DESCRIPTION OF PARTICULAR EMBODIMENTS

Figure 1A:
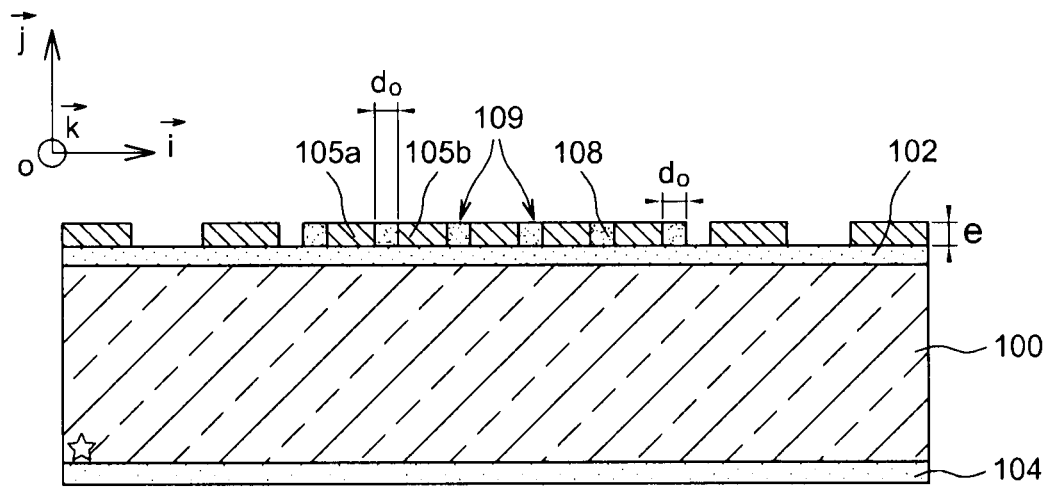
FIGS. 1A and 1B illustrate a first example of arrangement of the humidity sensor of capacitive type, with at least one capacitor provided with electrodes in the form of combs and with a nanoporous dielectric material located between the teeth of the combs.
Figure 1B:
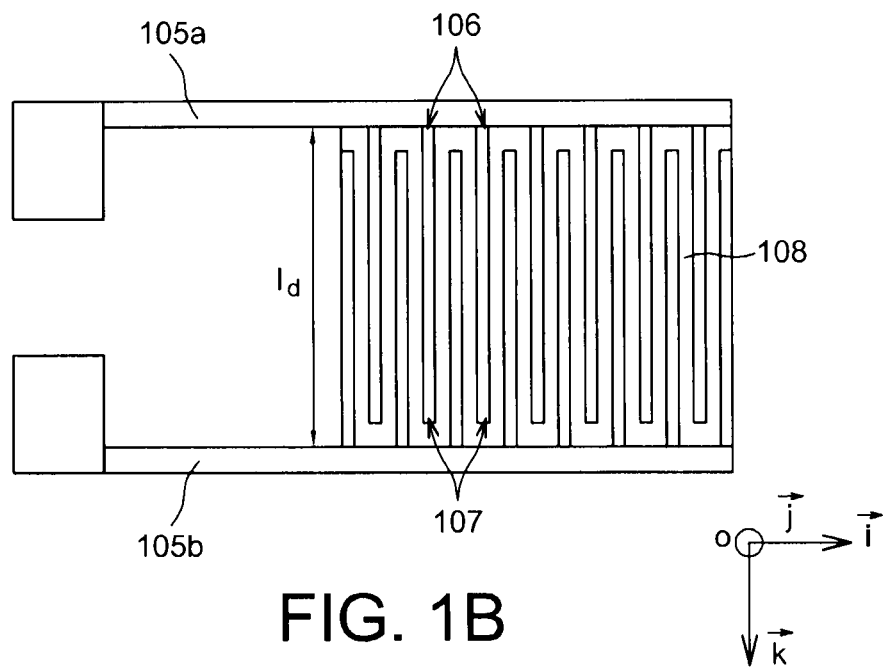

One example of a humidity sensor of capacitive type produced according to the invention is given in FIGS. 1A-1B.

The humidity sensor is formed on a substrate or wafer 100, which may be in semiconductor material e.g. Si.

The wafer 100 is coated with insulating layers 102, 104, respectively on its upper face and lower face. For example, these insulating layers 102, 104 may be formed by thermal oxidation of the substrate.

The sensor comprises electrodes 105a, 105b of at least one capacitor, which may each comprise a comb-shaped pattern. In FIG. 1B, the comb-shaped electrodes 105a, 105b have interdigitated teeth (respectively referenced 106 and 107).

The insulating layer 102 formed on the upper surface of the substrate can avoid the formation of short-circuits between the electrodes.

A nanoporous dielectric material 108 is positioned between electrodes 105a, 105b and in this example is distributed over the same plane as the latter. Therefore, the thickness e of the layer 109 of nanoporous dielectric material 108 and of the electrodes 105a, 105b is substantially equal (the thickness e being a dimension measured along a direction parallel to the vector $\vec{j}$ of the orthogonal reference [O; $\vec{i}$; $\vec{j}$; $\vec{k}$] defined in FIGS. 1A and 1B). For example, the layer 109 of nanoporous dielectric material 108 may have a thickness e of between 100 nanometers and 500 nanometers e.g. of the order of 150 nanometers.

When the humidity level changes in the surrounding atmosphere of the capacitor, the dielectric constant of the layer 109 of dielectric material 108 which absorbs humidity is modified in relation to the quantity of absorbed water. This variation may be substantial even if the humidity level is low, insofar as the dielectric constant of water ($\in$=80) is much higher than that of the chosen dielectric material 108.

The nanoporous dielectric material 108 may effectively have a dielectric constant $\in$ of less than 5, e.g. of the order of 3.

The dielectric material 108 has a large open porosity of 30% to 50% for example, with a pore size that is slightly larger than that of the water molecule which has a radius of 0.132 nm.

The nanoporous dielectric material 108 is a material designed with pores whose maximum radius is less than 2 nanometers. The mean radius of the pores of the nanoporous material 108 lies between 0.2 nanometers and 1.5 nanometers for example. The nanoporous material 108 may be in SiOCH or methylsilsesquioxane (MSQ).

The nanoporous material 108 may have been subjected to hydrophilic treatment using $N_2O$ plasma. With said treatment, it is possible to obtain pores in the nanoporous material 108 of the order of 0.6 nanometers for example if the nanoporous material 108 is SiOCH. An open porosity of the order of 32% may, for example, be obtained by means of said treatment.

The hydrophilic treatment using $N_2O$ plasma allows a nanoporous material 108 to be obtained having pores of mean radius of the order of 0.7 nanometers for example if the nanoporous material 108 is MSQ. In this case, an open porosity of the order of 46% can also be obtained with this hydrophilic treatment.

In this arrangement, since the layer 109 of nanoporous dielectric material 108 does not project beyond the surface of the electrodes 105a, 105b, the variation in water contained in this dielectric 108 may be fully measured. The humidity is effectively entirely located between the teeth 106, 107 of the combs. The capacitance value of the capacitor depends upon the parameters indicated in the following formula:

$$C = \frac{\varepsilon_0 \varepsilon r S}{d_0} \quad (1)$$

Where:
S: the surface of the electrodes, (S=h*ld*Ne)
$d_0$: air gap or distance between the teeth of the electrodes,
$\in_0$: vacuum dielectric permittivity,
$\in r$: permittivity of the porous material,
e: thickness of the electrodes,
h: height of the teeth,
ld: length of comb teeth,
Nd: total number of comb teeth,
Ne: number of air gaps (Ne=Nd−1).

With said capacitor, the capacitance is all the higher, the shorter the value of the distance between the teeth 106, 107 of the combs. The air gaps may be of the order of 1 to 2 μm. The number Nd and length ld of the teeth of the combs may be designed for example to obtain a capacitor capacitance of the order of one or more pF, corresponding to a dielectric layer of the capacitor not containing any water.

Figure 2A:
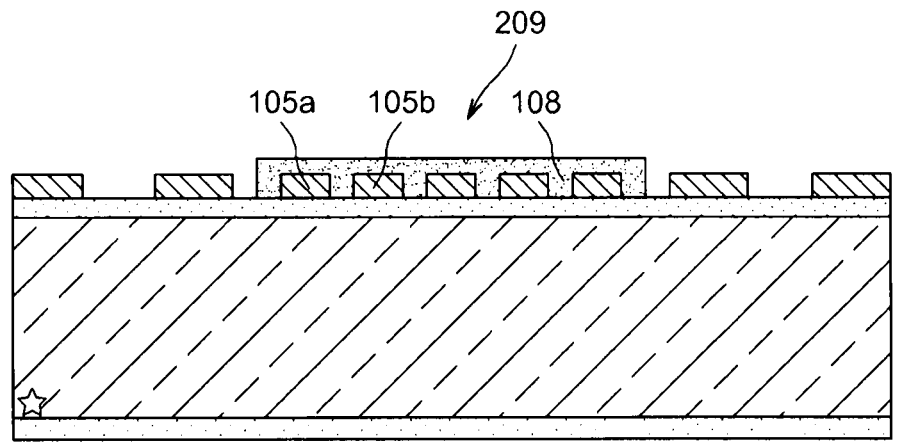
FIGS. 2A and 2B illustrate a second arrangement example of a humidity sensor of capacitive type, with at least one capacitor provided with comb-shaped electrodes, and with a nanoporous dielectric material arranged between and on the teeth of said combs.
Figure 2B:
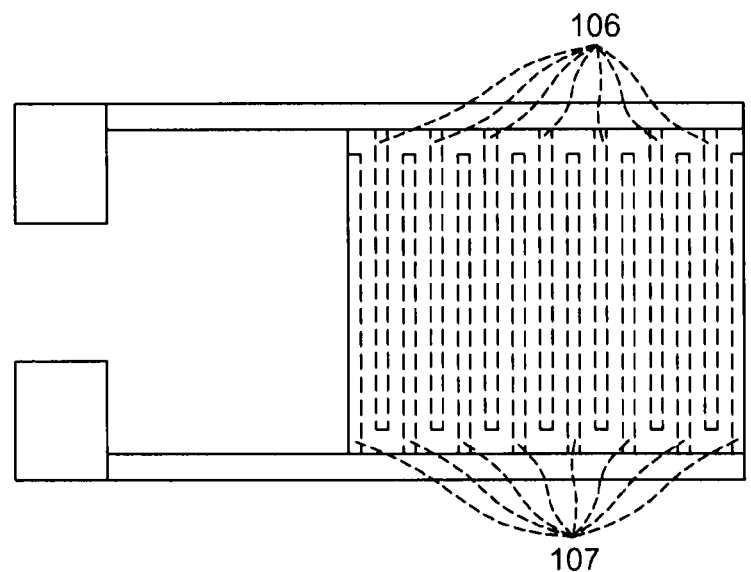

FIGS. 2A and 2B illustrate another example of a capacitive humidity sensor.

In this other example, the nanoporous dielectric material 108 has a different distribution to the one in the previously described example, and is in the form of a layer 209 covering the teeth 106, 107 of the electrodes 105a and 105b (FIGS. 2A and 2B). The high open porosity of the material 108 allows water to diffuse between the teeth 106, 107.

By "open porosity" is meant that the pores of the material are able to communicate with one another and with the outside of the material.

According to one example of the dimensions of either one of the sensors just described, the length of the comb fingers may be of the order of 1,000 μm for example, the number of interdigitated fingers may be of the order of 300 for example, the distance of the air gaps may be of the order of 1.5 μm for example.

Figure 3A:
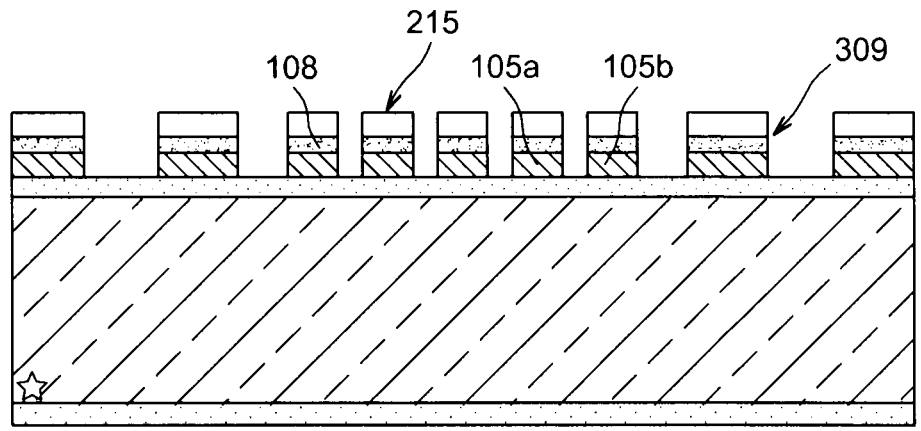
FIGS. 3A and 3B illustrate a third arrangement example of a humidity sensor of capacitive type, with at least one capacitor provided with comb-shaped electrodes and with a floating electrode, the sensor comprising a nanoporous dielectric material located between the floating electrode and the comb-shaped electrodes.
Figure 3B:
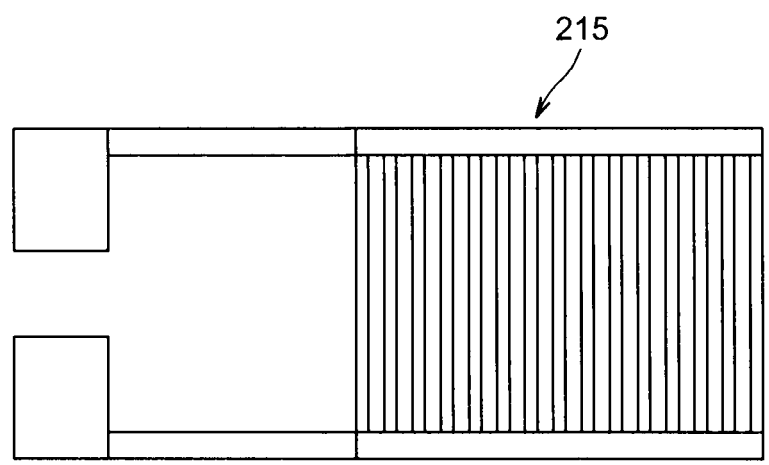

In FIGS. 3A and 3B, another example of embodiment of the humidity sensor is given. In this example, the sensor further comprises an additional electrode, in the form of a floating electrode 215. The floating electrode 215 is provided above a portion of the electrodes 105a, 105b and in particular above the teeth 106, 107 of the combs.

In this case, the nanoporous dielectric material 108 may be distributed in the form of at least one block 309 resting on the electrodes 105a, 105b and positioned between the latter and the floating electrode 215. The composition and thickness of the floating electrode 215 are designed so that it is permeable to humidity.

The floating electrode 215 may be in Cr or Au for example and be of narrow thickness, e.g. of between 5 nanometers and 20 nanometers, for example of the order of 10 nanometers. The upper floating electrode 215 is designed to have a thickness allowing electric conductivity to be reached whilst maintaining sufficient permeability.

The floating electrode 215 may have a pattern or follow a pattern reproducing the pattern of part of the electrodes 105a and 105b, in particular that part of the electrodes 105a, 105b that is comb-shaped.

The block 309 of dielectric material 108 may also follow the pattern of the floating electrode 215.

Said sensor is designed so that humidity is able to enter into the porous dielectric 108 through the floating electrode 215 and via the sides of the block 309 of porous dielectric 108.

Figure 4A:
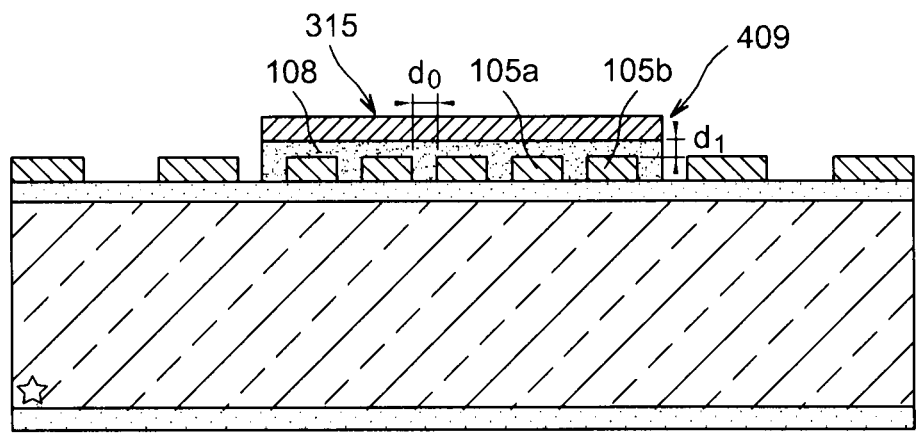
FIGS. 4A and 4B illustrate a fourth example of arrangement of a humidity sensor of capacitive type, with at least one capacitor provided with comb-shaped electrodes, the sensor comprising a porous dielectric material located between a rectangular floating electrode and the comb-shaped electrodes.
Figure 4B:
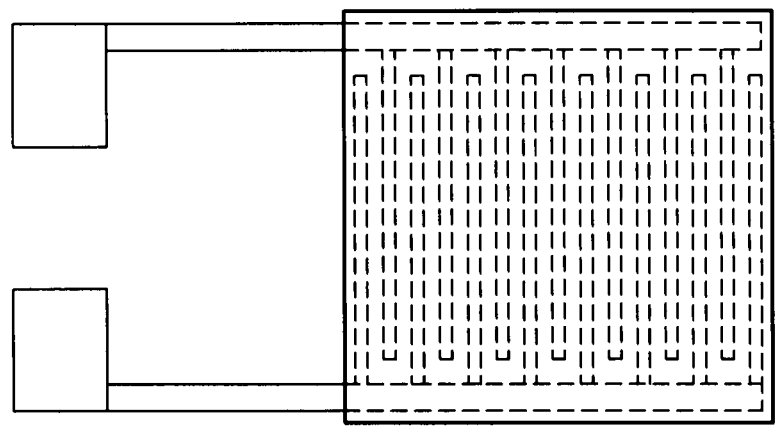

In FIGS. 4A and 4B, another example of a sensor is given.

In this example, the sensor is provided with an upper permeable floating electrode 315 formed of a rectangular metal region which rests upon a block 409 in the porous dielectric material 108. The block 409 of dielectric material may follow the same pattern as that of the electrode 315, and cover the comb-shaped electrodes 105a, 105b.

In this case, the humidity enters into the dielectric 108 through the permeable electrode 315.

A variation in capacitance of the capacitor due to a variation in humidity level in the dielectric 108 has two components: a first component due to the variation in dielectric constant of the material 108 in a space $d_0$ lying between the teeth 106, 107 of the electrodes 105a, 105b, and another component due to the variation in dielectric constant of the dielectric material 108 in the space $d_1$ between the combs of the electrodes 105a, 105b and the floating electrode 315.

Figure 5A:
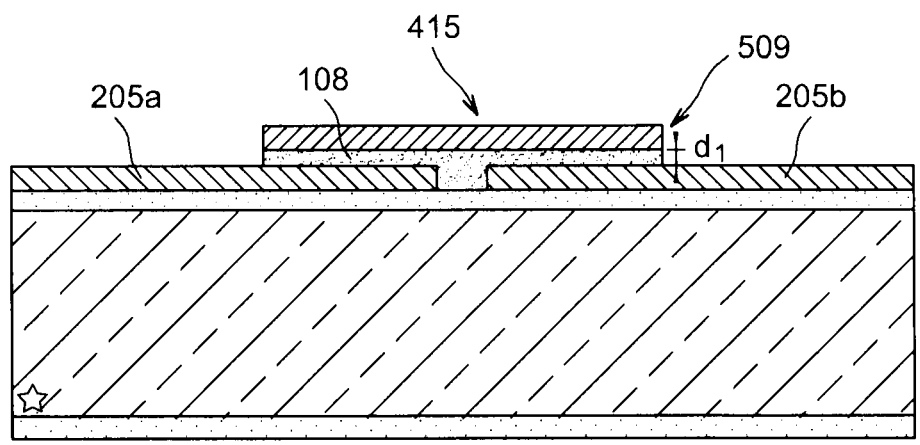
FIGS. 5A and 5B illustrate a fifth arrangement example of a humidity sensor of capacitive type, with at least one capacitor provided with rectangular-shaped electrodes and with a floating electrode, the sensor comprising a nanoporous dielectric material positioned between the floating electrode and the comb-shaped electrodes.
Figure 5B:
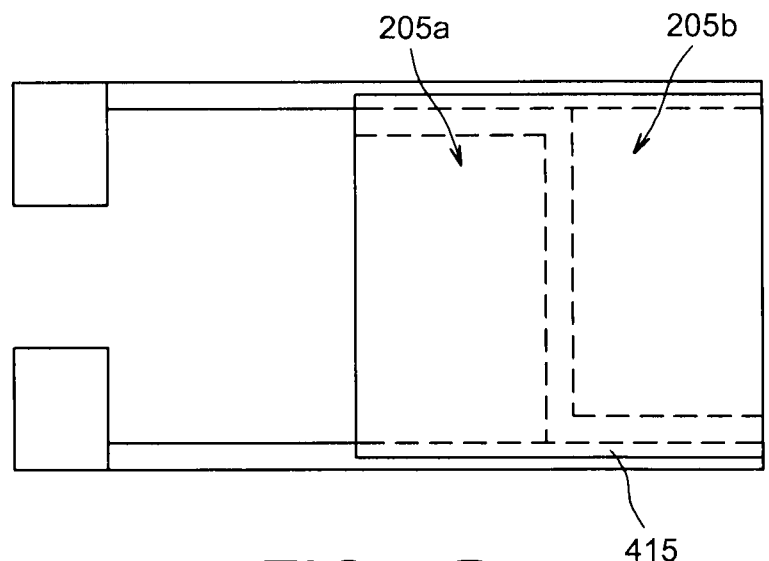

Another example of a sensor is illustrated in FIGS. 5A and 5B.

In this example, two electrodes 205a, 205b of rectangular shape are formed on the insulating layer 102 of the substrate 100 and are separated by a region of a block 509 of nanoporous dielectric material 108. The block 509 of nanoporous dielectric material 108 also covers part of the electrodes 205a, 205b. Upon the block 509 of dielectric material 108, there also rests a permeable floating electrode 415 which may be of rectangular shape. In this example, the variation in capacitance due to humidity has a single component due to the variation in $\in$ along space $d_1$ between the top of the lower electrodes 205a, 205b and the top of the floating electrode 415.

To implement any of the above-described devices, the nanoporous dielectric material 108 may have been formed by deposition e.g. by Chemical Vapour Deposition (CVD) for the case in which this material is SiOCH for example, or by spin coating followed by annealing if this material is MSQ for example.

Next, one or more patterns are formed in the material 108 e.g. by forming a mask such as a resin mask and etching through this mask.

Removal of the resin mask may be performed with a stripping technique. This stripping may use an RIE plasma method in oxygen/argon mixture to remove part of the resin, then a helium/hydrogen mixture to remove the remainder of the resin without damaging the nanoporous material.

If the nanoporous material 108 is SiOCH, this may be formed using an approach comprising the co-depositing of a precursor of an organic matrix and a pore-forming sacrificial material by chemical vapour deposit using plasma (PECVD), followed by treatment to remove the pore-forming organic phase. A SiOCH material 108, provided with pores of mean radius of the order of 0.8 nanometers for example and porosity of the order of 34% can then be obtained.

If the nanoporous material 108 is MSQ, this may be formed using a solution of polymethyselsisquioxane (MSQ) mixed with an organic pore-forming agent containing methacrylate in a solution of methylpropyleneglycol acetate (PGMEA) deposited by spin coating for example.

A MSQ material 108 provided with pores of mean radius of the order of 1.2 nanometers for example and porosity of the order of 46% can thus be obtained.

Once the material 108 is deposited, hydrophilic treatment can be carried out to create hydrophilic sites on the nanoporous material 108.

For this purpose, the treatment may use an oxidizing plasma e.g. $N_2O$ plasma, or $CO_2$ plasma, or $O_2$ plasma, pure or diluted in Ar, $N_2$, He. In this manner, it is possible to reduce the size of the pores and of open porosity.

The material thus treated has a very large developed surface i.e. a total surface of pores which allows a very large number of adsorption sites to be obtained which will be occupied by the first adsorbed layer or Langmuir layer (mono-molecular layer covering a surface) and which is generally complete with relative humidity of <20% HR. The pores of the material 108 can be saturated with relative humidity of less than 50 or 55%.

A MSQ or SiOCH-based nanoporous material 108 allows very high sensor sensitivity to be achieved for very small quantities of water (of the order of several ppm or several ppb).

The sensitivity of the sensor according to the invention, comprising a layer of the nanoporous material 108, is greater than that of prior art sensors in mesoporous or microporous material, in particular for measurements of low humidity levels ranging from 0 to 20% RH for example, notably from 0 to 10% RH.

The nanoporous material 108 has a specific adsorption mechanism. This adsorption mechanism can be mono and poly-molecular.

The quantity of water adsorbed in the pores of the nanoporous material 108, can be estimated using the following "Brunauer, Emmett, Teller" equation (BET):

$$\frac{N}{Nm} = \frac{1}{1 - P/Po} - \frac{1}{1 + (P/Po)(Q - 1)}$$

N: absolute quantity of adsorbed gas (in moles)
Nm: quantity of adsorbed gas per monolayer (in moles)

$$Q = \exp\left[\frac{(q - qc)}{RT}\right]$$

q: adsorption heat
qc: condensation heat
R: ideal gas constant
T: temperature
P: pressure
P0: saturation vapour pressure at Temperature T.

This equation describes polymolecular adsorption and can be used to define the number of adsorbed layers at a given pressure.

Since the nanoporous material 108 has pores with a mean radius of the order of one nanometer, this material is saturated well before 50 to 55% RH is reached.

According to one aspect of the invention, a capacitive humidity sensor such as described previously, and comprising a nanoporous, hydrophilic dielectric material 108 can be used for example to detect leaks in components or in encapsulated or sealed electronic devices, e.g. in an accelerometer or pressure sensor protected by a cover.

As indicated previously, the porous dielectric material 108 may be SiOCH for example.

One example of the method to fabricate a layer of nanoporous SiOCH material will now be described.

This material can be formed using PECVD (Plasma Enhanced Chemical Vapour Deposition), preferably using a so-called "pore-forming method".

For this purpose, a two-phase material can be deposited: a first phase containing Si, O, C, H intended to form the backbone of the porous dielectric material, and a second organic so-called "pore-forming" phase containing C, H and optionally O, which acts as sacrificial phase. The sacrificial phase is degraded during treatment, leading to the formation of a thin nanoporous layer.

The precursors used for depositing may be diethoxymethylsilane for example for the phase intended to form the backbone, and Trivertal® manufactured by P.C.A.S., for the pore-forming phase.

According to one example, the deposition conditions for a capacitive sensor adapted to wafers of 200 mm may be as follows: pressure of the order of 7 torr for example, power of the order of 350 W, deposit temperature of the order of 200° C. for example. Annealing in an oven may then be conducted for example at a temperature of the order of 450° C., for a time of the order of 8 h for example.

Figure 6A:
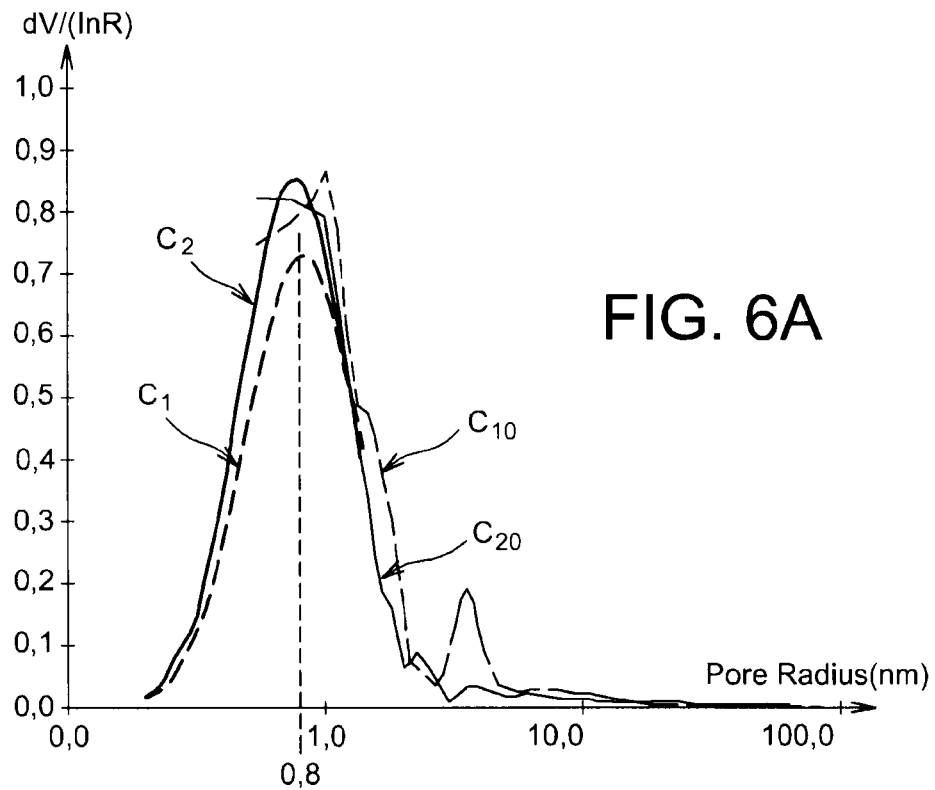
FIGS. 6A and 6B show curves of statistical pore distribution in a SiOCH dielectric.

It is possible to obtain an open porosity, measured on a SiOCH layer with thickness of 0.35 μm for example, of the order of 34% with a mean pore radius of the order of 0.8 nm (FIG. 6A for example).

The layer of SiOCH nanoporous material may then undergo treatment so that it becomes hydrophilic.

In FIG. 6A, curves C1 and C2 give the pore radius distribution in a porous SiOCH material, for adsorption (curve C1) and desorption (C2) respectively.

The curves represent the statistical distribution of pores of different radii in relation to radius. The tip of these Gauss curves is centred on the mean pore radius.

Curve C1 shows this distribution calculated from adsorption measurements of a measuring liquid such as Toluene.

Curve C2 shows this distribution calculated from desorption measurements of a measuring liquid such as Toluene.

Curves C10 and C20 correspond to the pore size calculated using Kelvin's law.

The curves represent a statistical distribution of pore size, $dV/d(lnR)$ being the probability of the presence of the pores of given radius.

The treatment to create hydrophilic sites on the nanoporous material 108 may use $N_2O$ plasma for example to apply hydrophilic treatment to the nanoporous material.

After treatment, an open porosity of the nanoporous layer of the order of 32% can be obtained, with a mean pore radius of the order of 0.6 nanometers.

Figure 6B:
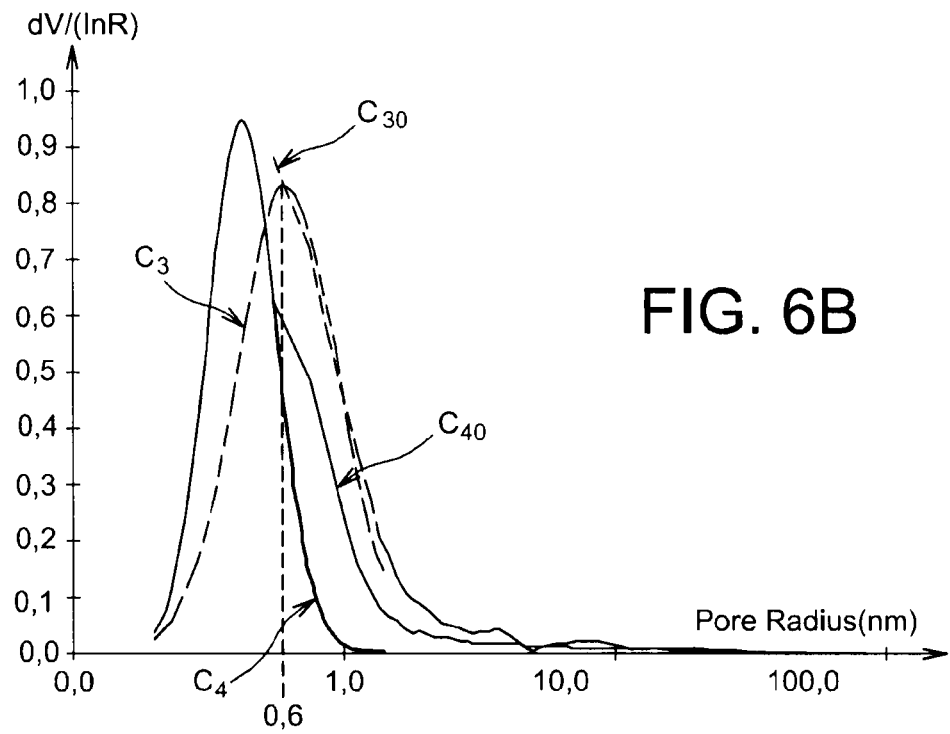

In FIG. 6B, measurement curves C3 and C4 give the distribution of pore radii in a SiOCH porous material, once this material has undergone hydrophilic treatment, with respect to adsorption measurements (curve C3) and desorption measurements (curve C4) respectively.

Curves C30 and C40 correspond to pore size calculated using Kelvin's law.

The curves represent a statistical distribution of pore size, $dV/d(lnR)$ being the probability of the presence of the pores of given radius.

One example of a method to fabricate a layer of MSQ nanoporous material will now be described.

This material may be deposited for example using a spin coating method to deposit a solution containing a sacrificial material, e.g. poly-methyselsisquioxane and an organic pore-forming agent containing methacrylate, the whole in solution in a solvent e.g. PGMEA (Propylene Glycol Monomethyl Ether Acetate).

Annealing of the material on a hot plate can then be performed, for example at a first temperature e.g. 100° C. for an initial period for example of 30 s, then at a higher temperature e.g. 200° C. for a time of the order of 4 min for example to remove the solvent.

The sample is then placed in an oven for 1 h for example at a temperature of the order of 450° C. The treatment applied leads to total extraction of the pore-forming phase and the creation of pores in the material having a radius of less than 2 nanometers.

It is possible to obtain an open porosity, on a layer of thickness 0.35 μm, of the order of 46.1% for example with mean pore radius of the adsorbed layer of the order of 2.2 nm for example.

Figure 7A:
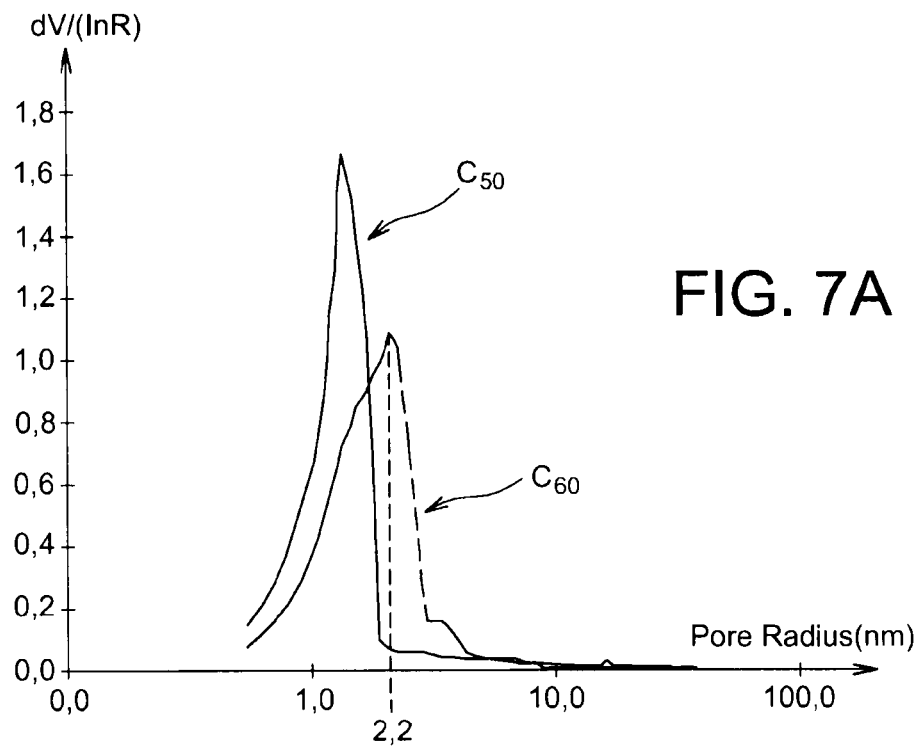
FIGS. 7A and 7B show curves of statistical pore distribution in a MSQ dielectric.

In FIG. 7A, curves C50 and C60 give the pore radius distribution in a porous MSQ material.

It is then possible to apply hydrophilic treatment to the MSQ material.

After this treatment, it is possible to obtain an open porosity of the order of 35.8% for example, with mean pore radius of the order of 0.7 nm.

Figure 7B:
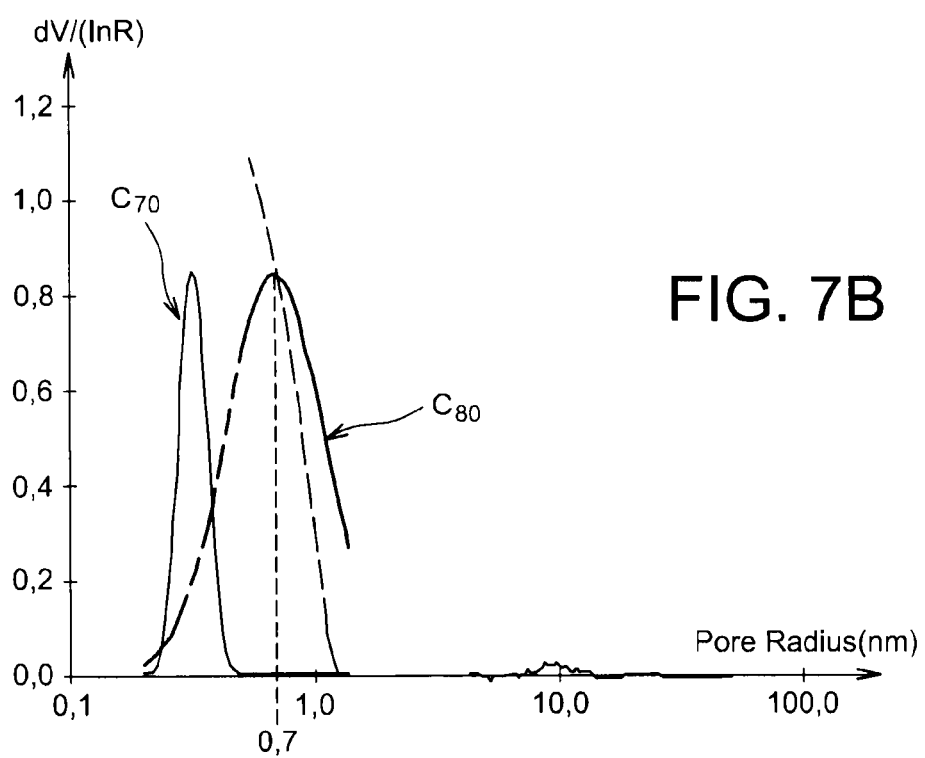

In FIG. 7B, curves C70 and C80 give the pore radius distribution in MSQ nanoporous material, after hydrophilic treatment, with respect to measurement of Toluene adsorption and desorption respectively.

The above-mentioned nanoporous materials have a large developed surface i.e. a large pore surface and a high number of absorption sites.

A layer of MSQ dielectric material having a pore percentage of the order of 35.8% for example, and mean pore diameter of 1.4 nm, can be obtained.

A layer of nanoporous material 108, such as previously described, can be saturated with water as soon as 2 to 3 molecular layers of water are adsorbed for relative humidity values of <55%.

Therefore, a low increase in the surrounding humidity of the nanoporous material 108 allows a very large increase to be obtained in the dielectric constant of the layer of dielectric material 108, due to a strong concentration of water in the nanoporous material, even at low pressure.

This allows very early detection of a leak in the cavity of an encapsulated component left in a medium in which the humidity is that of the ambient atmosphere, and which generally corresponds to values of the order of 20 to 60% RH.

One example of a method to fabricate a humidity sensor of capacitive type according to the invention will now be described with reference to FIGS. 8A to 8H.

Figure 8A:
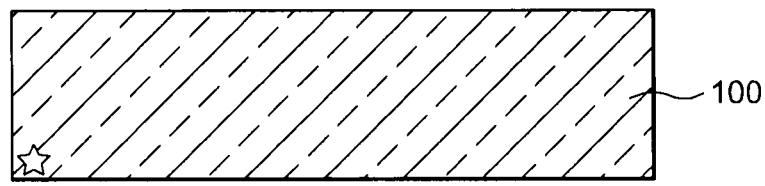
FIGS. 8A to 8H illustrate a second example of a method to fabricate a humidity sensor of capacitive type comprising a nanoporous dielectric material.

The starting material of this method may be a substrate 100 or wafer 100 in semiconductor material, for example a Si wafer having a thickness of the order of 525 μm, and which may comprise a polished front face (FIG. 8A).

Figure 8B:
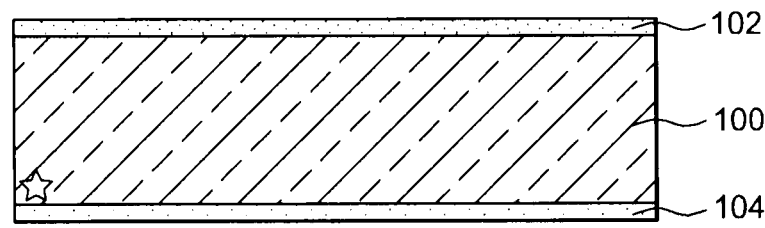

An insulating layer is formed on each of the faces of the wafer. These insulating layers 102, 104, may be formed by oxidizing the substrate 100 for example and may have a thickness of the order of several micrometers, for example of the order of 2 μm (FIG. 8B).

One or more electrodes of at least one capacitor are then formed.

Figure 8C:
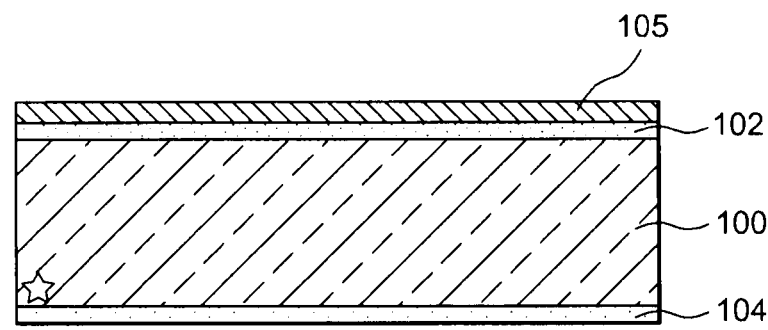

For this purpose, first a metallic layer 105 is deposited on the insulating layer 102 (FIG. 8C). The deposit may be AlCu for example of thickness of the order of 150 nanometers, or a stack formed of a layer of Cr of thickness 10 nanometers for example and a layer of gold e.g. of the order of 150 nanometers.

Next, patterns are formed in the metallic layer 105, for example by photolithography followed by etching.

Figure 8D:
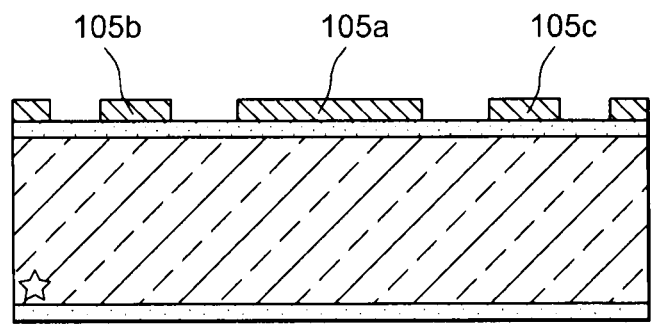

Coplanar electrodes 105a, 105b, e.g. in the form of inter-digitated combs may thus be formed (FIG. 8D).

Figure 8E:
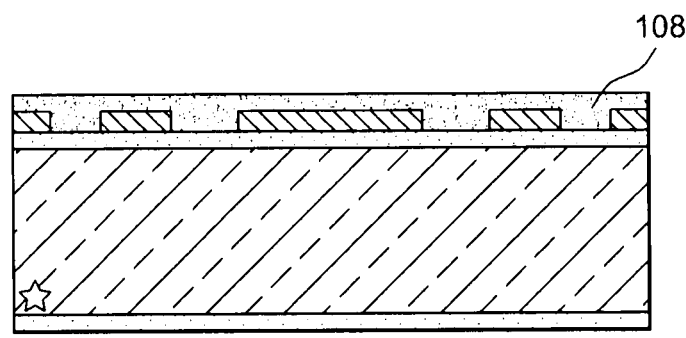

Next, a layer of nanoporous dielectric material 108 is formed on the metallic electrodes, e.g. having a thickness of between 250 and 500 nanometers. The porous dielectric material 108 may be in SiOCH or MSQ for example, and may be deposited by PECVD for example (Plasma Enhanced Chemical Vapour Deposition) (FIG. 8E).

The nanoporous material is formed and provided with pores of radius lying between 0.6 nanometers and 2 nanometers.

The nanoporous material may be formed using a method such as described in the foregoing.

Hydrophilic treatment of the nanoporous material 108 is then conducted using $N_2O$ plasma.

Figure 8F:
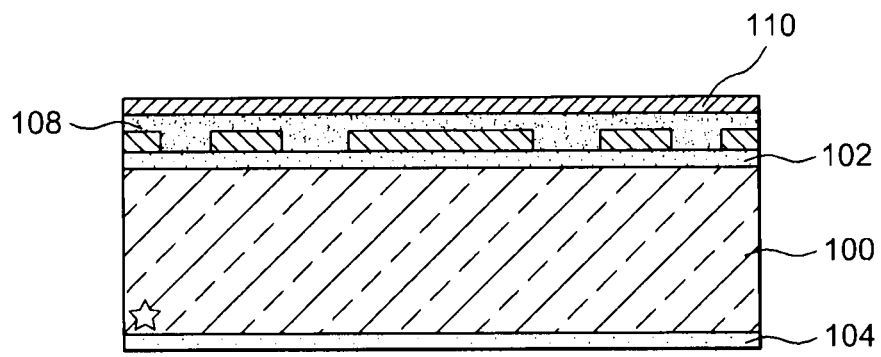

Next, thin layer of metallic material 110 is deposited, e.g. in gold or Cr. The thin layer of metallic material 110 may have a thickness of between 5 and 20 nanometers, e.g. of the order of 10 nanometers (FIG. 8F). The thickness and the material of the metallic layer 110 may be designed so that this layer is permeable to humidity.

A layer of gold of thickness of the order of 10 nanometers for example is not fully continuous.

A layer of Cr, of thickness of the order of 10 nanometers, in particular when deposited by vacuum evaporation, is constrained and has a tendency to cause cracks in the material on which it is deposited. Said cracks can allow the entry of water vapour therein.

Next, at least one upper electrode is formed in the layer of metallic material 110 of the capacitor. This is performed by etching the layer in metallic material 110 and the layer of nanoporous material.

Figure 8G:
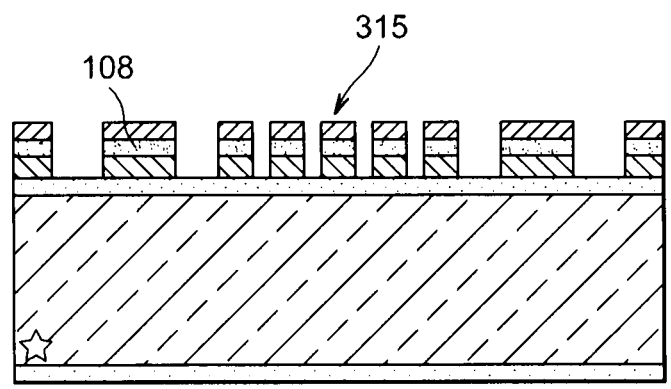

According to one possibility, comb-shaped patterns comprising interdigitated teeth can be formed in these layers 108, 110 (FIG. 8G).

Figure 8H:
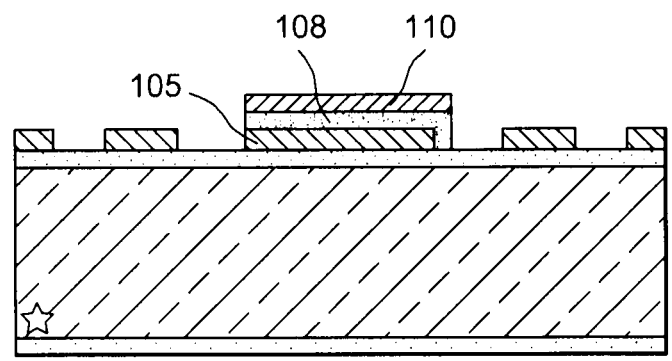

According to one variant, the electrodes may be in the form of rectangular patterns (FIG. 8H).

One variant of the example of a method to fabricate a humidity sensor of capacitive type according to the invention, just described, will now be described with reference to FIGS. 9A to 9H.

The starting material of this method may also be a substrate 100 or wafer 100 in semiconductor material on which insulating layers 102, 104 are formed on each side.

Next, (FIG. 9A), a layer of nanoporous dielectric material is formed on the metallic electrodes, having a thickness of between 250 and 500 nanometers for example. The porous dielectric material may be SiOCH or MSQ for example, and may be formed for example using a method such as described above.

The nanoporous material is formed with pores of radius between 0.6 nanometers and 2 nanometers.

Hydrophilic treatment is then applied to the material, using $N_2O$ plasma for example. Oxidation may occur over the entire surface of the pores.

Figure 9A:
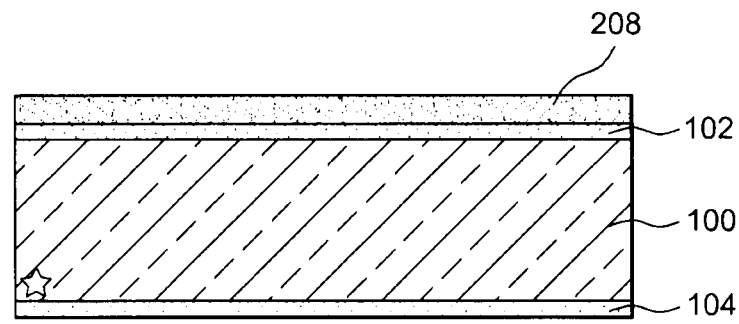
FIGS. 9A to 9F illustrate a second example of a method to fabricate a humidity sensor of capacitive type comprising a nanoporous dielectric material.
Figure 9B:
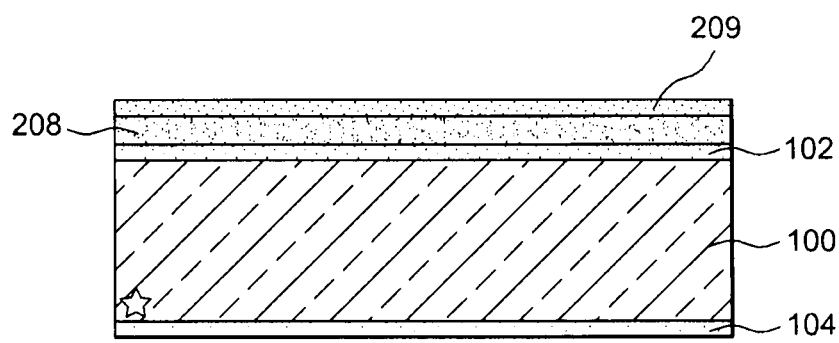

An insulating layer 209 is then formed on the layer of porous material 208. The insulating layer 210 may be $SiO_2$-based e.g. of TeOs type and may have a thickness of the order of 100 nanometers for example (FIG. 9B).

Figure 9C:
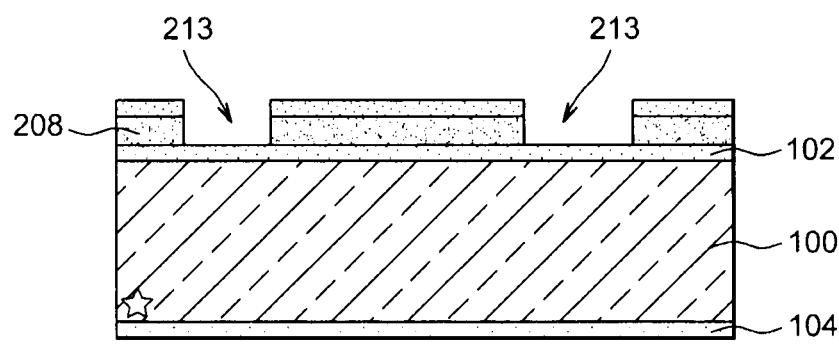

A plurality of openings 213 is subsequently made in the insulating layer 209 and in the layer of porous material 208, to expose the insulating layer 102 (FIG. 9C).

Figure 9D:
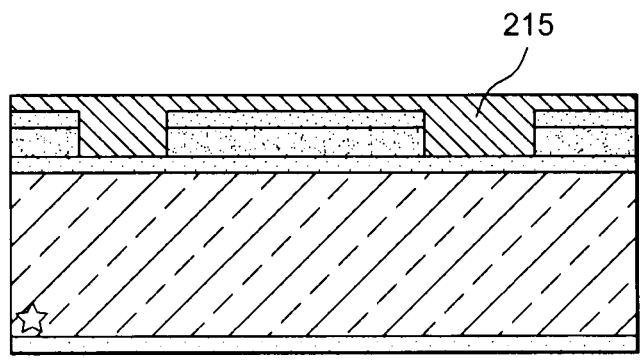

The openings are then filled with a metallic material 215, e.g. AlCu or Cu. The thickness of the metallic material may lie between 450 nanometers and 800 nanometers for example (FIG. 9D).

Figure 9E:
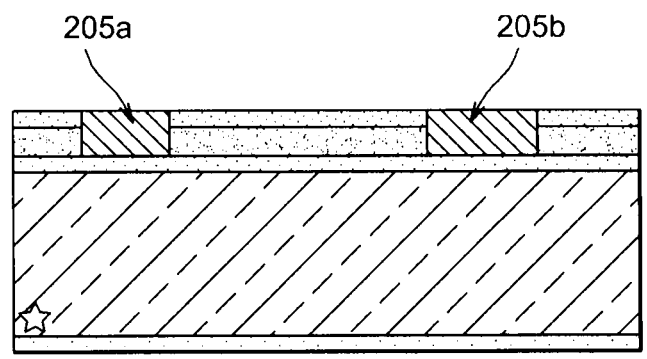

Polishing e.g. chemical mechanical polishing (CMP) is performed next to remove a thickness of metallic material 215 projecting beyond the openings. For example, a thickness of the order of 200 nanometers can be removed to form metallic electrodes 205a, 205b of a capacitor (FIG. 9E).

Figure 9F:
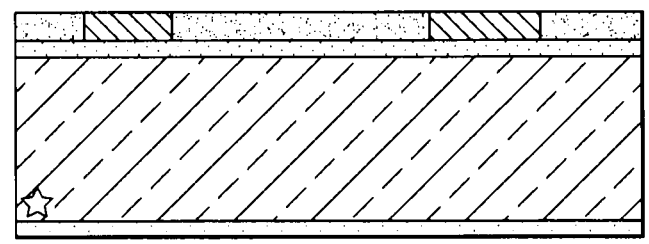

The insulating layer 209 can then be removed (FIG. 9F).

A differential measuring device provided with at least one first capacitor, comprising the nanoporous dielectric material 108, and at least one second capacitor comprising a dielectric material that is scarcely porous or non-porous and used as reference, may also be used to obtain measurements of greater precision.

Figure 12:
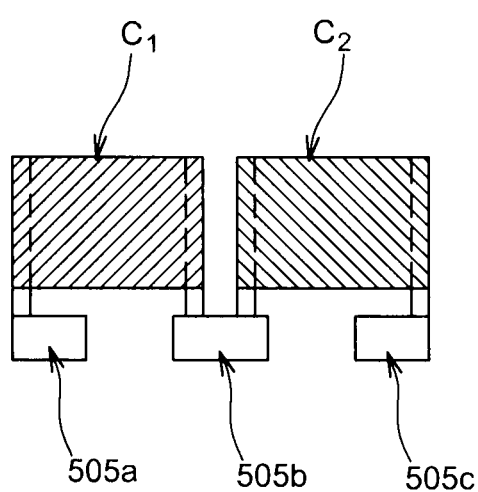
FIG. 12 illustrates an example of a differential device for measuring humidity, comprising a capacitive sensor with nanoporous dielectric and a capacitor with non-porous dielectric.

FIG. 12 illustrates an example of said device. In this example, a first capacitor $C_1$ is provided with a layer of nanoporous dielectric material (not shown in FIG. 22) such as MSQ or SiOCH, comprising pores of radius less than 2 nanometers and which may have been subjected to oxidizing hydrophilic treatment such as treatment with $N_2O$. The nanoporous dielectric is positioned between a first electrode 505a and a second electrode 505b, the second electrode 505b being a common electrode acting as reference electrode and shared by a second capacitor $C_2$.

The second capacitor $C_2$ is provided with a layer of another, non-porous, dielectric material, such as $SiO_2$ of TEOS type or a polymer of polyethersulfone type. By non-porous material is meant a material which does not comprise any open porosity.

The other dielectric material of the second capacitor $C_2$ is positioned between the common electrode 505b and another electrode 505c. The second capacitor $C_2$ is thus formed of a dielectric material whose dielectric properties are not modified by low variations in humidity and in particular between 0 and 500 ppm. The second capacitor $C_2$ acts as reference capacitor.

Therefore, when there is a variation in humidity, the value of the first capacitor $C_1$ changes, whilst the second capacitor remains invariable. To measure variation in humidity, the variation $C_2-C_1$ can be taken into account over the range 0 to 500 ppm.

With said differential measuring device, it is possible to overcome so-called "surface" parasitic phenomena and which are due for example to humidity on the electrodes and/or conductor lines. The dielectric material of the reference capacitor $C_2$ can be deposited using LPCVD for example (Low Pressure Chemical Vapour Deposition) from a liquid source of tetraethylorthosilicate and oxygen, the reaction taking place at a temperature of the order of 380° C.

A sensor according to the invention, can be used to detect leaks in encapsulated components, in particular electronic or microelectronic components or microsystems, for example in sensors of accelerometer, gyrometer or pressure sensor type protected by a cover generally in silicon sealed by a bead of resin, fusible glass or eutectic alloy or by an integrated cover in polysilicon.

For these types of components generally vacuum or $N_2$ encapsulated, the capacitor provided with a layer of nanoporous dielectric material can allow the detection of leaks on and after the $1^{st}$ ppm.

A humidity sensor according to the invention can be used to measure a quantity of water vapour contained in a gas or in the atmosphere of a sealed or closed component.

The component may be a MEMS component e.g. an accelerometer or gyrometer or seismometer.

The applications of a sensor according to the invention are multiple. Among these applications, in addition to the detection of humidity in sealed components, the following may be cited: the measurement of humidity in the ceramics industry to control the drying of items before firing, measurement of humidity in the paper industry, food industry, electronics industry and in fields in which drying or preferably low humidity levels are controlled.

To optimize performance levels in terms of sensitivity of a sensor according to the invention integrated in an encapsulated or sealed component, the humidity of the nanoporous dielectric material is desorbed before sealing or encapsulating, since a porous material contains a quantity of water which may be high in an ambient atmosphere. This desorption may depend on atmospheric humidity which can be <30% RH for example in cold weather in winter, and for example >60% RH in summer. Said desorption may be performed by vacuum heating for example e.g. at a temperature of the order of 200° C. and pumping.

Different results of sensitivity tests conducted on examples of capacitive humidity sensors according to the invention are described below.

Tests were conducted at a temperature of the order of 23° C. by adding air in stages under increasing pressure, with relative humidity content of the order of 50%, to an enclosure initially placed under a vacuum after heat treatment of the order of 200° C. for a time of the order of 10 minutes for example. Each device was tested using apparatus of 4284A LCR type by Hewlett Packard to plot curves of variation in capacitance $\Delta C/C$, in relation to the concentration of humidity.

Figure 10:
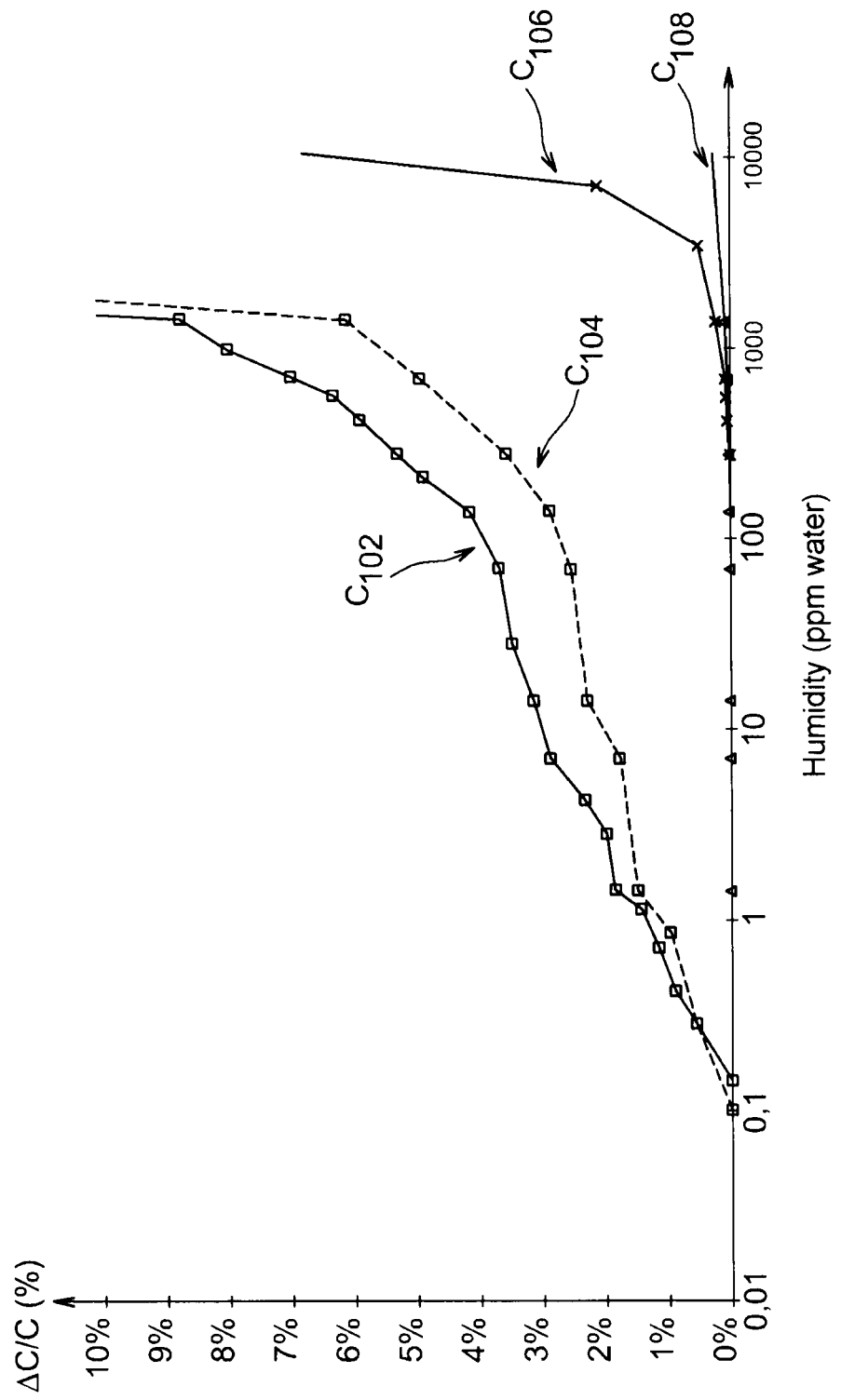
FIGS. 10 and 11 illustrate different results of tests conducted on examples of humidity sensors produced according to the invention.

In FIG. 10, the curves $C_{102}$, $C_{104}$ represent tests at a frequency of 1 kHz, respectively conducted on a capacitive sensor according to the invention formed of MSQ nanoporous hydrophilic dielectric, and on a capacitive sensor according to the invention of similar structure but whose nanoporous hydrophilic dielectric is SiOCH.

By way of comparison, the curve $C_{106}$ illustrates the sensitivity of a similar sensor in terms of arrangement, but provided with a TeOS dielectric, whilst curve $C_{108}$ illustrates the sensitivity of a sensor provided with a polymer-based dielectric of polyethersulfone type.

Figure 11:
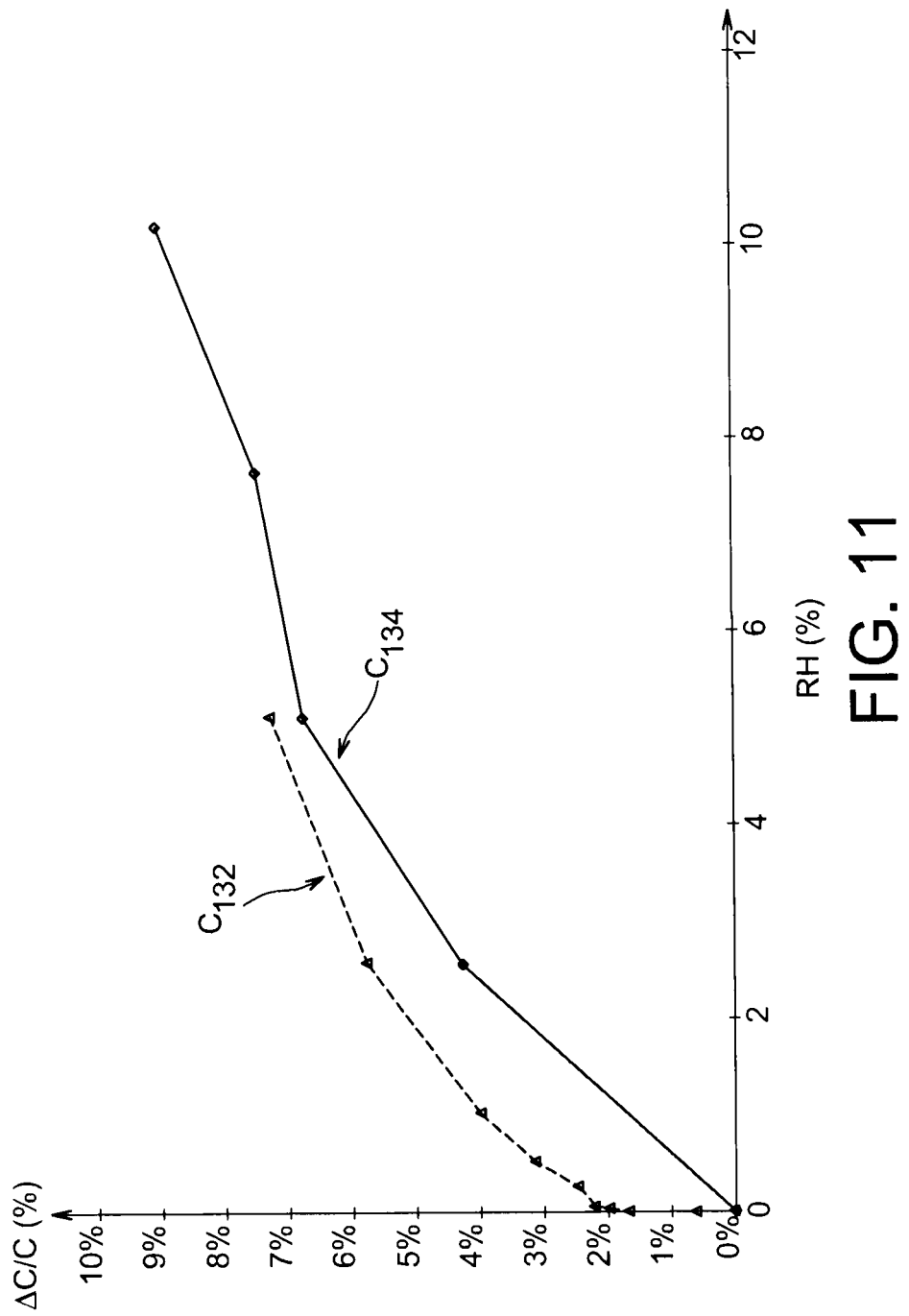

FIG. 11 gives capacitance variation curves $C_{132}$, $C_{134}$, in relation to relative humidity of a SiOCH capacitive humidity sensor respectively tested in a moist air atmosphere, and in a nitrogen atmosphere at a pressure of 800 mbar in which moist air containing a percentage of relative humidity of the order of 50% was added in stages and under increasing pressure.

The invention claimed is:

1. A humidity sensor of capacitive type, comprising:
   at least one first electrode and at least one second electrode; and
   at least one nanoporous dielectric material between the first electrode and the second electrode, the nanoporous dielectric material comprising pores with radius of less than 2 nanometers, the nanoporous dielectric material further comprising hydrophilic sites, the nanoporous dielectric material being MSQ or SiOCH.

2. The humidity sensor of capacitive type according to claim 1, the nanoporous dielectric material comprising hydrophilic sites on a surface thereof, including at least one of SiO sites, SiOH sites, and radical Si sites.

3. The humidity sensor of capacitive type, according to claim 1, further comprising:
   at least one floating electrode permeable to humidity resting upon the nanoporous material and positioned facing the first electrode and the second electrode.

4. A device for measuring or detecting humidity comprising:
   a sensor of capacitive type according to claim 1; and
   at least one capacitor including a common electrode with the capacitive sensor, the capacitor comprising a non-porous dielectric material.

5. The device according to claim 4, the non-porous dielectric material being a silicon oxide of TEOS type.

6. A device for detecting humidity in a sealed component comprising a device according to claim 4.

7. A device for detecting humidity in a sealed component comprising a sensor according to claim 1.

8. The device according to claim 1, wherein the nanoporous dielectric material has an open porosity between 30% and 50%.

9. A method to fabricate a humidity sensor of capacitive type, comprising:
   forming on a substrate at least one first electrode and at least one second electrode;
   forming at least one nanoporous dielectric material at least between the first electrode and the second electrode, the nanoporous dielectric material comprising pores with a radius of less than 2 nanometers, the nanoporous dielectric material being MSQ or SiOCH; and
   hydrophilic treatment of the dielectric material.

10. The method according to claim 9, wherein, after formation of the nanoporous dielectric material, further comprising hydrophilic treatment by oxidizing plasma of the dielectric material.

11. The method according to claim 10, the plasma being $N_2O$ plasma.

12. The method according to claim 9, further comprising fabrication of at least one floating, humidity-permeable electrode on the nanoporous material, and positioned facing the first electrode and the second electrode.

13. The method according to claim 9, wherein the nanoporous dielectric material has an open porosity between 30% and 50%.

* * * * *